(12) United States Patent
Stuber et al.

(10) Patent No.: US 6,230,039 B1
(45) Date of Patent: May 8, 2001

(54) MAGNETIC RESONANCE IMAGING METHOD AND SYSTEM WITH ADAPTIVELY SELECTED FLIP ANGELS

(75) Inventors: Matthias Stuber, Brookline; Rene Botnar, Chestnut Hill, both of MA (US)

(73) Assignee: Philips Electronics North America Corporation, New York, NY (US)

( * ) Notice: Subject to any disclaimer, the term of this patent is extended or adjusted under 35 U.S.C. 154(b) by 0 days.

(21) Appl. No.: 09/536,943

(22) Filed: Mar. 28, 2000

(51) Int. Cl.[7] .................................................. A61B 5/00
(52) U.S. Cl. ......................... 600/410; 324/309; 324/307
(58) Field of Search ..................... 600/410, 413, 600/419; 324/307, 309, 306

(56) References Cited

U.S. PATENT DOCUMENTS

| | | | |
|---|---|---|---|
| 4,937,526 | 6/1990 | Ehman et al. | 324/309 |
| 5,069,213 | 12/1991 | Polczynski | 128/633 |
| 5,307,014 | 4/1994 | Laub | 324/306 |
| 5,652,513 | 7/1997 | Liu et al. | 324/306 |
| 5,842,989 | * 11/1999 | Zur | 600/410 |
| 5,977,796 | * 11/1999 | Bornert et al. | 324/306 |

OTHER PUBLICATIONS

Pauly et al., "A k–Space Analysis of Small–Tip–Angle Excitation", Information Systems Laboratory, Stanford University, Dec. 7, 1987.

Sachs et al., "Real–Time Motion Detection in Spiral MRI using Navigators", MRM 32:639–645, 1994, The Information Systems Laboratory, Department of Electrical Engineering, Stanford University, Stanford, California, pp. 36–49.

Wang et al., "Algorithms for Extracting Motion Information from Navigator Echoes", MRM 36: 117–123, 1996, Diagnostic Radiology, pp. 117–123.

Wood et al., "Suppression of Respiratory Motion Artifacts in Magnetic Resonance Imaging", Medical Phys. 13 (6), Nov./Dec. 1986, pp. 794–805.

Liu et al., "A Monitoring, Feedback, and Triggering System for Reproducible Breath–Hold MR Imaging"MRM 30:507–511, 1993, Magnetic Resonance Laboratory, department of Diagnostic Radiology, Mayo Clinic and Foundation.

* cited by examiner

*Primary Examiner*—Marvin M. Lateef
*Assistant Examiner*—Eleni Maria Mantis Mercader
(74) *Attorney, Agent, or Firm*—John F. Vodopia

(57) ABSTRACT

This invention relates to methods and apparatus for magnetic resonance (MR) imaging of moving parts of a patient in which flip angles for the excitation of nuclear magnetization are adaptively selected during image data acquisition in order to minimize artifacts. In particular, the flip angles are selected so that a smooth distribution of signal-strengths in k-space results even though the order of phase-encoding gradients is also adaptively selected in dependence of the measured instantaneous state of motion of the moving part. The invention also includes MR apparatus for practicing the described methods and software for controlling an MR apparatus to practice the methods.

19 Claims, 5 Drawing Sheets

MAGNETIC RESONANCE IMAGING METHOD AND SYSTEM WITH ADAPTIVELY SELECTED FLIP ANGLES

BACKGROUND OF THE INVENTION

1. Field of the Invention

The present invention relates to methods and systems for magnetic resonance (MR) imaging of moving parts of a patient with reduced motion artifacts, in particular to MR imaging protocols in which both the magnetic field gradients and the flip angles ($\alpha$) for exciting nuclear magnetization are adaptively selected.

2. Description of the Related Art

Motion, notably due to or induced by cardiac or respiratory motions, is unavoidable in many clinical MR imaging situations. Without correction, MR images of moving parts of a patient are well-known to contain various confusing artifacts, such as ghost images, which can easily lead to clinical misinterpretation of the MR images.

In one known method for correcting such motion artifacts, after MR signals are collected, the displacement of the moving part is measured, such as by an MR navigator protocol. The collected MR data is then retrospectively discarded, i.e., not used for image reconstruction, if the subsequently measured displacement exceeds a threshold value. See, e.g., Sachs et al., 1994, Magnetic Resonance in Medicine 32:639–645.

However, this method, known as motion "gating", has the problem of lengthening data collection times in proportion to the fraction of time during which the displacement of the moving part exceeds the threshold value. Also the steady state of nuclear magnetization must be maintained. If the steady state is not maintained, MR signals measured when the displacement is below threshold will have varying signal strengths. Varying signal strengths introduce unpredictable modulations in k-space that are also well-known to lead to artifacts in the visible image.

An improvement to the gating method, referred to herein as motion-adaptive gating ("MAG"), attempts to shorten the data collection period by collecting MR data with less stringent boundary conditions than required by simple gating. According to this method, without significant loss of image quality, data generated from phase encoding gradients with larger time-integrals (stronger gradients) can be acquired at greater displacements, such as at greater respiratory or diaphragmatic displacements, as long as data generated from phase-encoding gradients with smaller time-integrals are acquired at smaller displacements. Then, it is only for a comparatively smaller fraction of time, when the displacement becomes very large, that no useable MR signals at all can be collected. The MAG method is described in U.S. patent application Ser. No. 08/795,119 filed Feb. 7, 1997, now U.S. Pat. No. 5,977,769.

Although the MAG method may reduce data collection times, it can also lead to increased artifacts due to increased, unpredictable signal-strength modulations in k-space. It will be immediately appreciated that in MAG the actual sequence of phase-encoding gradients can be highly disordered. Depending on the motion's course, MR signals adjacent in k-space can be acquired at unpredictable and widely different times during data acquisition. Unless the strength of the MR signals is carefully and smoothly controlled throughout data collection, modulations will be superimposed on k-space having an unknown structures. Random modulation components blurs the point spread function; periodic components produce ghosts, possibly leading to such misinterpretations as focal stenosis. The requisite careful control of MR signal strengths is, however, difficult and problematic.

Therefore, since both gating and, especially, motion-adaptive gating, although reducing motion artifacts, may introduce further artifacts due to uncontrolled and unpredictable modulation of signal strength in k-space, what is needed are simple and reliable MR methods and apparatus for also reducing or eliminating these further artifacts in order to achieve MR images with reduced motion artifacts in reduced times.

Citation of a reference herein, or throughout this specification, is not to be construed as an admission that such reference is prior art to the Applicants' invention of the invention subsequently claimed.

SUMMARY OF THE INVENTION

The object of the present invention is to provide methods and apparatus which overcome the above identified problems in, and satisfy the needs of, the art. In particular, it is an object of this invention to provide simple and reliable MR methods and apparatus for reducing or eliminating the artifacts due to uncontrolled or unpredictable modulation of signal strength in k-space introduced by gating, in particular by respiratory gating, and, especially, by motion-adaptive gating. Thereby, the present invention provides MR images of moving parts of a patient with improved image quality and in reduced scan times.

Generally, this object is achieved by methods of MR imaging according to which, where the temporal order of phase-encoding gradients applied to generate MR images is non-deterministic, or unpredictable, or uncertain, or even random for whatever reason, resulting irregularities of the signal strength distribution in k-space are minimized by adaptively selecting the overall signal strength of the generated MR signals in at least partial dependence on the phase-encoding gradients to be applied so that a pre-determined and smooth signal strength distribution is achieved in k-space. MR signal strengths are selected by determining magnetization flip angles, or RF powers, applied to excite the MR signals.

In particular, in the preferred embodiment, non-deterministic temporal ordering of phase-encode gradients results from adaptive gating methods. These methods make use of the fact that lower spatial frequency components of k-space, which provide for overall image definition, are more susceptible to motion disturbance, while higher spatial frequency components, which provide for finer image details, are less susceptible to motion disturbance. Therefore, the methods of this invention, first, determine the instantaneous state of motion of the part of the patient being imaged, and, second, select the spatial frequency of the phase encoding gradients next to be applied so that the lower spatial frequency components are acquired when the state of motion is less, while the higher spatial frequency components can be acquired when the state of motion is greater.

In preferred embodiments, the state of motion is represented by displacements of a moving part of a patient being imaged from a reference position along the directions of the phase-encoding gradients of the MR data acquisition sequence. The spatial frequencies of the data to be acquired are represented by the time integral of the phase-encoding gradients applied.

Next, the strength of the MR signal that will be generated from the next imaging sequence is also adaptively selected in at least partial dependence on the instantaneous state of motion, or on the time-integral of the selected phase-encoding gradient, in order that the signal strength distribution throughout k-space will be have a smooth and slowly-varying pre-determined shape that minimizes artifacts. Flip angles, and RF powers, are determined to achieve the selected MR signal strength.

In preferred embodiments, the flip angles are chosen so that the overall signal strength decreases smoothly and monotonically from the center of k-space to its periphery and is circularly symmetric. Further, for increased accuracy, the flip angles are selected in further dependence on the expected state of longitudinal magnetization just before the RF pulse. Further, the expected state of longitudinal magnetization can be determined by neglecting the effects of residual transverse magnetization, or for increased accuracy, it can be determined by taking these effects into account.

Finally, the following preliminary matters are set forth. Generally, "k-space" is taken herein to be a spatial-frequency domain in which an MR signal is sampled along a trajectory, the sampled values yielding the inverse Fourier transformed values of the magnetization distribution excited in the body. The trajectory in the k-space is determined by the time integral of temporary "magnetic gradient fields" over a time interval from the excitation of the nuclear spins to the actual instant of measurement of the MR signal.

Nuclear magnetization is excited in the body by RF pulses which cause the net magnetization vector to have components transverse to the steady magnetic field. The "flip angle ($\alpha$)" is taken herein to represent the strength of this excitation, preferably by measuring the angle of rotation of the net magnetization vector from the longitudinal direction.

Although, for simplicity, the invention is primarily described herein in an embodiment directed to two-dimensional (2D) imaging, the invention is even more applicable to three-dimensional (3D) imaging. Accordingly, as used herein, "phase-encoding gradients" are taken to encompass both the 2D embodiment, in which there is a single stepped gradient along a single direction, and the 3D embodiment, in which there are two stepped gradients along two orthogonal directions.

Further, also for simplicity and without limitation, both the 2D and 3D embodiments are described in terms of trajectories in k-space consisting of lines perpendicular to the phase-encode directions generated. Alternatively, this invention is adaptable to other known types of trajectories sampling k-space having the property that each trajectory in samples only a limited range of spatial frequencies. Since motion disturbs lower spatial frequencies in k-space more than higher spatial frequencies, the sensitivity of each trajectory having this property to motion of the object being imaged can be determined in advance. Thereby, from measurement of the instantaneous state of motion of the object, as in the linear 2D and 3D embodiments, those trajectories can be selected and generated that will have acceptable motion artifacts.

As used herein, the "steady state" of nuclear magnetization is a state created by certain fast (with repeat times short compared to relaxation times) imaging sequences during which both the longitudinal and the transverse components of the nuclear magnetization exhibit a steady temporal state.

BRIEF DESCRIPTION OF THE DRAWING

Other objects, features and advantages of the present invention will become apparent upon study of the following detailed description when taken in conjunction with the appended drawing, wherein.

DETAILED DESCRIPTION OF THE PREFERRED EMBODIMENTS

In the following, first presented is an exemplary embodiment of an MR apparatus for practicing the MR methods of the present invention for imaging a moving object. Following are descriptions of preferred and alternative embodiments of the methods of the present invention, including their exemplary implementation as computer hardware and/or software.

An Exemplary MR-Apparatus of the Present Invention

Figure 1:
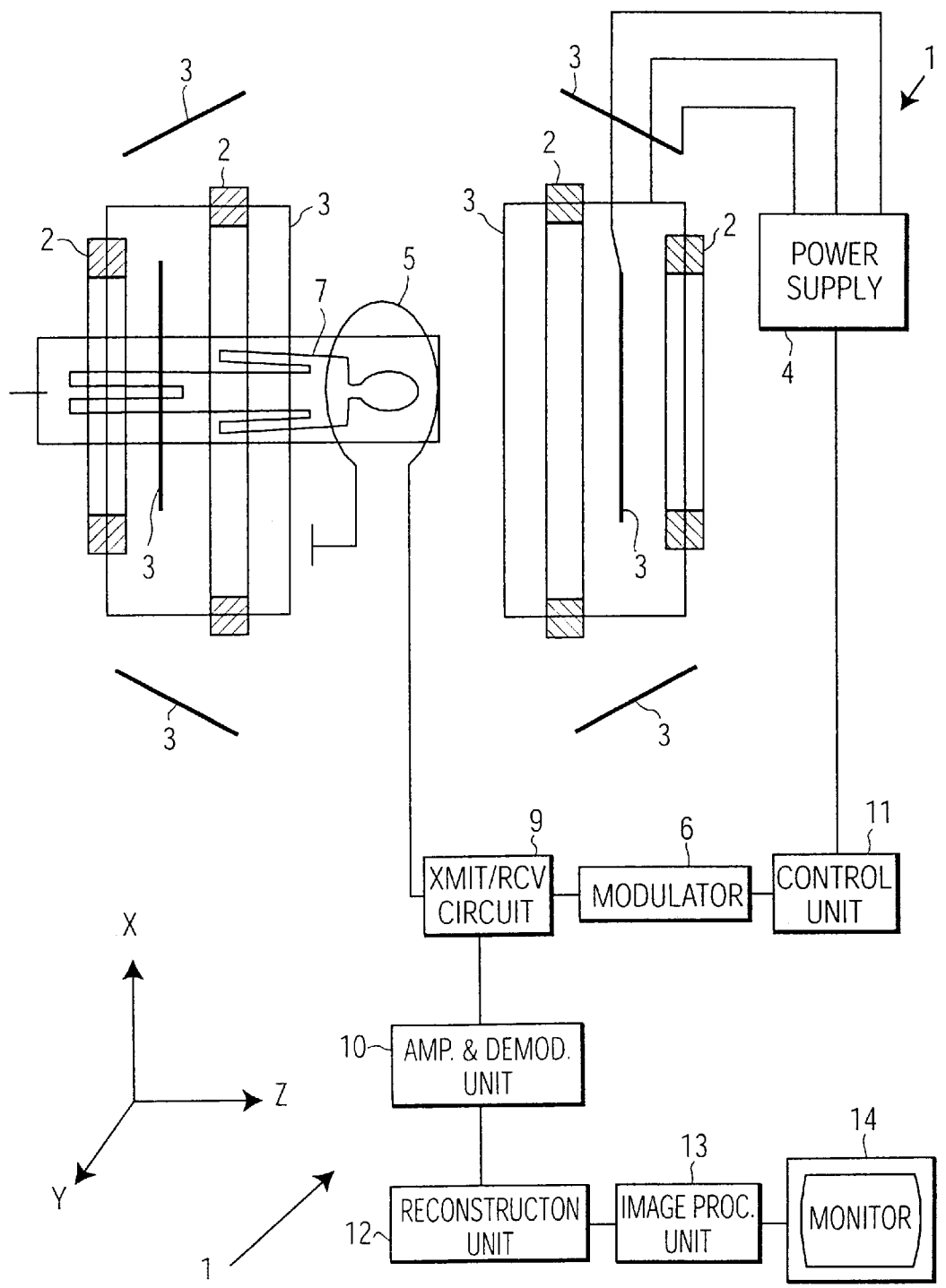
FIG. 1 illustrates an exemplary embodiment of an MR apparatus for practicing the present invention.

FIG. 1 illustrates MR apparatus 1 for practicing the present invention. MR apparatus 1 includes main magnet system 2 for generating a steady magnetic field in an examination zone of the MR apparatus. The z-direction of the coordinate system illustrated corresponds to the direction of the steady magnetic field generated by magnet system 2.

The MR apparatus also includes gradient magnet system 3 for generating temporary magnetic fields $G_x$, $G_y$ and $G_z$ directed in the z-direction but having gradients in the x, y or z directions, respectively. With this magnetic gradient system, magnetic gradient fields can also be generated that do not have directions coinciding with the main directions of the above coordinate system, but that can be inclined thereto, as is known in the art. Accordingly, the present invention is not limited to directions fixed with respect to the MR apparatus In this application, for ease of description, the directions x, y and z (and the gradients along these directions) are used for the read direction, the phase encode direction and slice-selection direction (or second phase-encode direction for 3D imaging), respectively.

Magnet systems 2 and 3 enclose an examination zone which is large enough to accommodate a part of object 7 to be examined, for example a part of a human patient. Power supply means 4 feed the gradient magnet system 3.

The MR apparatus also includes an RF transmitter system including RF transmitter coil 5, which generates RF pulses in the examination zone and is connected via transmitter/receiver circuit 9 to RF source and modulator 6. RF transmitter coil 5 is arranged around the part of body 7 in the examination zone. The MR apparatus also comprises an RF receiver system including an RF receiver coil which is connected via transmitter/receiver circuit 9 to signal amplification and demodulation unit 10. The receiver coil and the RF transmitter coil 5 may be one and the same coil.

The MR apparatus also includes amplification and demodulation unit 10, which, after excitation of nuclear spins in a part of the body placed within the examination space by magnetic gradient fields and RF pulses and after reception of the resulting MR signals by the receiver coil, derives sampled phases and amplitudes from the received MR signals. Image reconstruction unit 12 processes the received MR imaging signals to, inter alia, reconstruct an image by methods well-known in the art, such as by Fourier transformation. By means of image processing unit 13, the reconstructed image is displayed, for example, on monitor 14. Further, the image reconstruction unit can optionally process MR navigator signals to determine the displacement of a portion of the patient.

The MR apparatus also includes control unit 11 that generates signals for controlling the RF transmitter and receiver systems by means of modulator 6, the gradient magnetic field system by means of power supply means 4, image reconstruction unit 12 and image processing unit 13. In a preferred embodiment, the control unit (and other control elements in the MR apparatus) are implemented with programmable elements, such as one or more programmable signal processors or microprocessors, communicating over busses with supporting RAM, ROM, analog signal interfaces, control interfaces, interface to computer-readable media and so forth. These programmable elements are commanded by software modules loaded into RAM or ROM, written according to well-known methods to perform the real-time processing required herein, and loaded from computer-readable media, such as magnetic disks or tapes, or optical disks, or network interconnections, or so forth. In a less preferred embodiment, the control unit that directs an MR apparatus for practicing the present invention can be implemented with dedicated electronic components in fixed circuit arrangements. In this case, these dedicated components are arranged to carry out the method described above.

In particular, the control unit commanded by its loaded software causes the generation MR signals by controlling the application of MR sequences, which comprise RF-pulses and temporary magnetic gradient field pulses. These sequences are generated according to the methods of the present invention as subsequently described, and generally include 2D and 3D imaging sequences and optionally navigator sequences for determining the displacement of the patient is gathered.

Furthermore, according to the present invention, the MR apparatus also optionally includes various other units (not illustrated) from which the state of motion of the part of the patient being imaged can be measured. These can include sensors directly indicating the instantaneous state of motion of the part of the patient being imaged, such as a chest belt for directly indicating chest displacement during respiration, or MR-active micro-coils whose position can be tracked, or optical means, or ultrasound means, or so forth. These units can also include sensors indirectly indicating the instantaneous state of motion of the part of the patient being imaged. For example, electrocardiogram and peripheral pulse sensors measure the temporal progress of the cardiac cycle, and permit inference of the actual state of motion of the heart from knowledge of cardiac displacements associated with each phase of the cardiac cycle. When these sensors are present to measure the state of motion, the control unit need not generate navigator sequences.

The Methods of the Present Invention

Turning now to the general methods of this invention, in a preferred embodiment, first, the instantaneous state of motion of the part of the patient being imaged is determined. Because of the relatively longer time interval between steps of the phase-encoding gradients compared to the relatively shorter time interval during which M signals are actually read, the relevant aspect of the state of motion is preferably its instantaneous amplitude (or displacement) in any direction (or directions) in or in-between the phase encoding gradient (or gradients).

This invention can use any devices provided with an MR apparatus that measure the relevant instantaneous amplitudes (or displacements) of motion of the part of the patient being imaged. In a preferred embodiment, the state of motion, i.e., the amplitude (or displacement) of motion in any direction, can be directly determined from MR navigator signals.

Figure 2A:
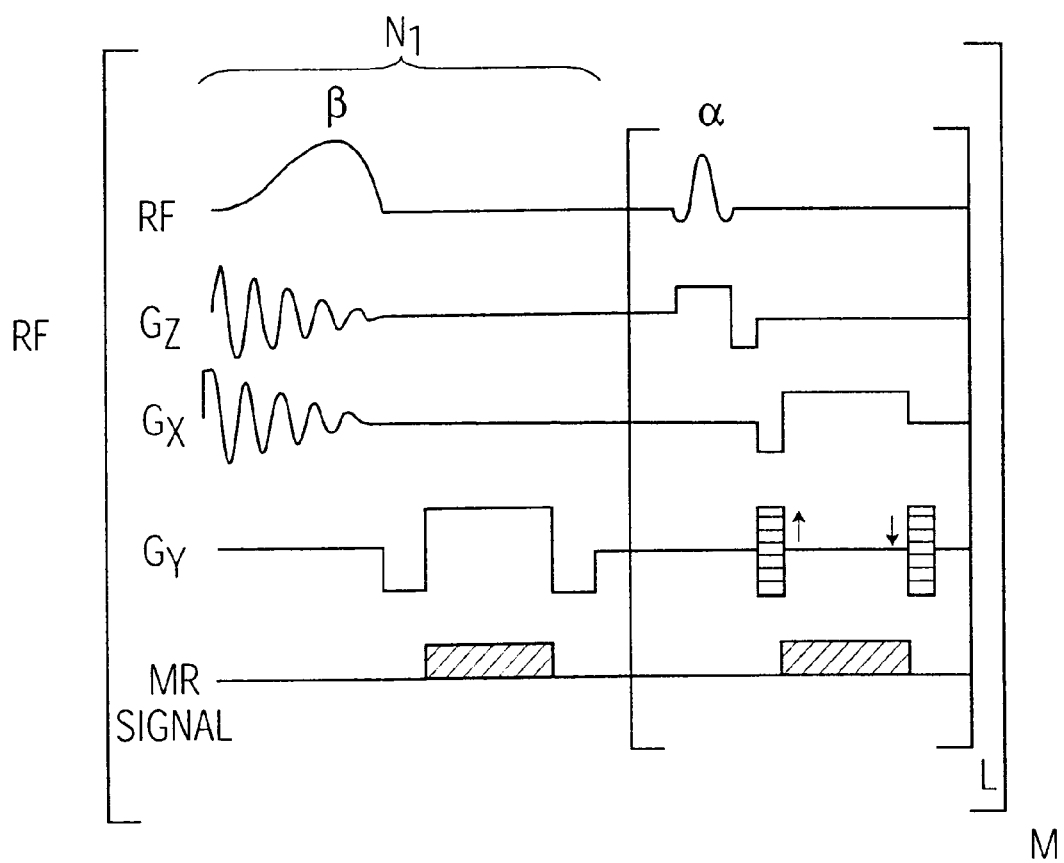
FIGS. 2A–B illustrate exemplary MR imaging sequences for practicing the present invention.
Figure 2B:
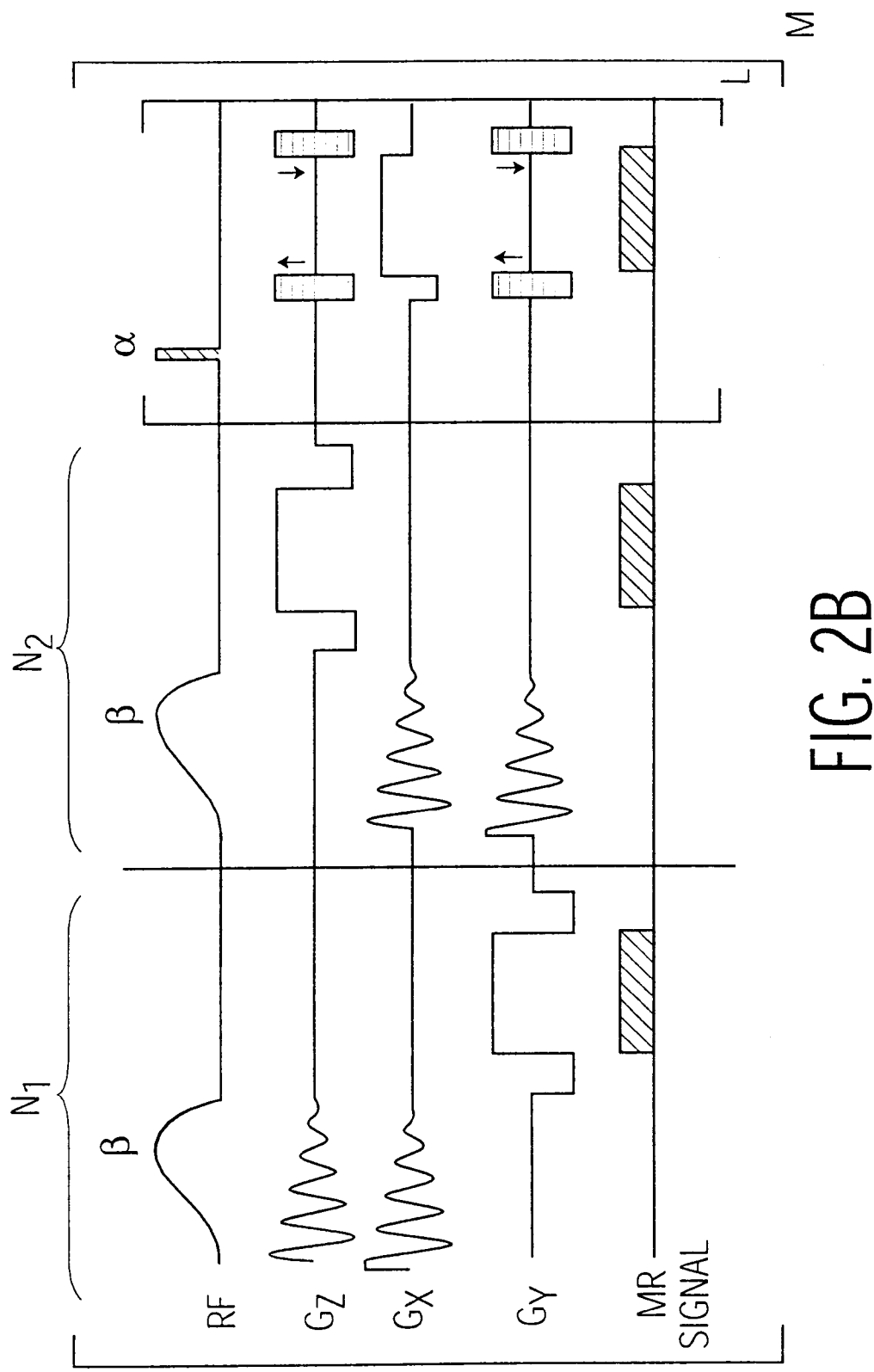

Before proceeding to the further steps, in particular to the adaptive selection of the next phase-encoding gradient and flip angle in dependence on the instantaneous state of motion, exemplary MR sequences for the practice of this invention are described with reference to FIGS. 2A and 2B, illustrating exemplary 2D and 3D sequences, respectively. First, FIG. 2A illustrates an exemplary sequence having an initial navigator portion, $N_1$, followed by a final imaging portion having L repeats of a 2D field-echo imaging sequence.

In this exemplary sequence, initial navigator portion, $N_y$, commences by exciting nuclear magnetization in a thin pencil-shaped region parallel to the y-axis, or phase-encode axis, using two-dimensional RF pulse β (first line) in cooperation with oscillatory gradients $G_z$ (second line) and $G_x$ (third line). Two-dimensional excitation is well-known. See, e.g., Pauly et al., 1989, Journal of Magnetic Resonance 81:43–46. The pencil-shaped region is preferably chosen to extend through and beyond the part of the patient being imaged in order that displacement of the part can be unequivocally determined. An MR signal (fifth line) is subsequently generated from the pencil-shaped region by reading gradient, $G_y$, (fourth line), along the phase-encode axis. The amplitude, or displacement, of the part from a reference position, can be determined by, for example, reconstructing the spatial magnetization distribution followed by cross-correlation of the measured distribution with a reference distribution. Extraction of displacements from navigator signals is also well-known. See, e.g., Wang et al., 1996, Magnetic Resonance in Medicine 36:117–123.

Although FIG. 2A illustrates that the first navigator sequence measures amplitude along the y-axis, this invention is not so limited. The direction of first navigator measurement can in fact be along any axis, for example, the v-axis, which best describes the motion. In this case, the amplitude of motion along the v-axis is measured by exciting magnetization along the v-axis by a two-dimensional RF pulse combined with oscillatory gradients along the perpendicular u and w-axes which are both, in turn, perpendicular to the v-axis. Navigator signals are then generated by a read gradient along the v-axis. Gradients along arbitrary u, v, and w-axes are known to be easily generated by linear combinations of gradients along the x, y, and z-axes. Alternately, navigator information can be derived by excitation of a plane slice.

The final imaging portion of FIG. 2A illustrates an exemplary field-echo sequence. Nuclear magnetization in a slice is excited by slice-selective RF pulse α (first line) in the presence of slice-selection gradient $G_z$ (second line); next phase-encoding gradient $G_y$ (fourth line) is applied; and the MR image signal (fifth line) is acquired in cooperation with read gradient $G_x$ (third line). Selection according to the present invention of the flip angle α (or the needed RF power) and the time integral of the phase-encoding gradient ($G_y$) are described subsequently. In this exemplary sequence, a phase-encoding gradient with the reverse direction ("rewinder" gradient) is also applied after MR data collection in order that the steady state of nuclear magnetization not be disturbed by the phase-encoding gradient.

The 2D imaging sequence is repeated L times. L, which is typically three to eight, is selected so that there will be little significant motion of the imaged part of the patient during the L repeats. Finally, both the navigator and the imaging portions of FIG. 2A are M times until data necessary for image reconstruction is collected.

Turning to exemplary 3D imaging sequences, in one alternative 3D embodiment, the repeats of the 2D imaging sequence of FIG. 2A are simply replaced by repeats of a known 3D imaging sequence, such as the 3D field-echo imaging sequence illustrated in the final portion of FIG. 2B. The 3D sequence of FIG. 2B differs from the 2D imaging sequence of FIG. 2A in that stepped phase-encoding gradients are applied in two orthogonal directions, here along the y-axis (fourth line) and the z-axis (second line). Selection of flip angle α (or RF power) and the time-integrals of the two phase-encoding gradients is similar to the 2D case and is described subsequently. This 3D alternative is preferable where the motion of the moving part of the patient being imaged is primarily along a single (for example, the y) direction, and can be adequately measured by a single navigator sequence ($N_y$). It is also adaptable to situations where motions in other directions can be predicted from measurements along the single direction.

FIG. 2B illustrates another 3D embodiment, preferred where the moving part of the patient executes substantially uncorrelated motions in two or more directions, necessitating measurement of the amplitudes (or displacements) in both direction. Here, both displacements are determined from two navigator measurements, $N_1$ and $N_2$, along the two phase-encode directions.

This invention is not limited to the sequences illustrated in FIGS. 2A and 2B, but is adaptable to any other MR imaging sequence in which the overall strength of the generated MR signals can be controlled by the flip angle used to excite the MR signals. Further, this invention is not limited to the relation between the navigator sequences and the imaging sequences illustrated in FIGS. 2A and 2B. For example, navigator sequences can be interspersed in imaging sequences of any length as needed to accurately account for the instantaneous state of motion. Further the navigator sequence need not be along the directions of the encoding gradients. In fact, the $N_1$ and $N_2$ navigators can measure displacements along two arbitrary directions, perpendicular or not, which best describe the motion occurring. Additionally, the invention is adaptable to 3D imaging sequences combined with three navigator sequences which measure the amplitude of motion along general directions in space.

Now returning to description of the general methods of this invention, next, the phase-encoding gradients to be next applied, e.g., in the next repetition of the imaging sequence of FIG. 2A, are selected in dependence at least in part on the previously determined instantaneous state of motion of the part of the patient being imaged. Generally, for a given amplitude (or displacement) of motion along the phase-encoding direction, only phase-encoding gradients having a time integral (or spatial frequency) greater than a certain threshold can be applied, the greater the displacement the greater the time integral threshold. Equivalently, phase-encoding gradients having a given value can be applied only when the instantaneous amplitude of motion is less than this threshold. Thereby, phase-encoding gradients closer to the center of k-space are applied only when the instantaneous amplitude is relatively smaller.

Preferably, this dependence is represented by a relation which, for a given value of the time integral, specifies the threshold displacement along the phase-encoding direction at or below which application of the give phase-encoding gradient is permissible. More preferably, this relation specifies the threshold as a monotonic increasing function of the time integral.

Figure 3:
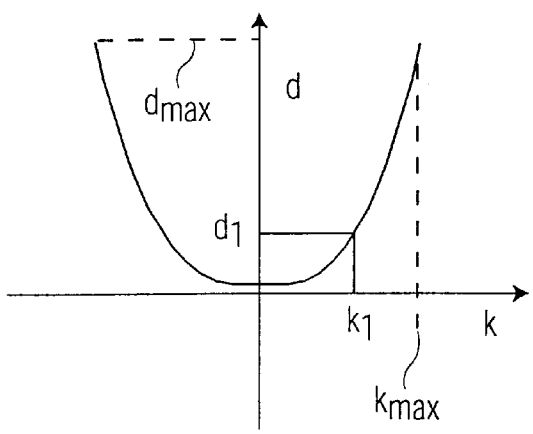
FIG. 3 illustrates a preferred relation between the time integral of a phase-encode gradient and the instantaneous displacement.

FIG. 3 illustrates an exemplary such relation. In this figure, the instantaneous displacement, d, is along the vertical axis, and the time integral of the phase-encoding gradient, k, is along the horizontal axis. Also, $k_{max}$, is the maximum time integral of the phase-encoding gradient, and $d_{max}$ is the maximum displacement beyond which MR signals should not be acquired at all. For example, time integral $k_1$ is permissible for displacements at or below $d_1$, while, equivalently, at displacement $d_1$ all time integrals from $k_1$ to $k_{max}$ are permissible. The function illustrated has the preferred cubic dependence of the displacement threshold on the time-integral threshold. See, e.g., U.S. patent application Ser. No. 08/795,119, filed Feb. 7, 1997 (now allowed).

In the case of 2D imaging sequences, the displacement measured along the phase encode direction determines the time integral threshold directly from this preferred relation (or its equivalent). In the case of 3D imaging sequences, the two displacements measured along each of the two phase-encode directions determine from the preferred relation (or its equivalent) two independent thresholds for the time integrals of the gradients along the two phase-encode directions, respectively. Also, in the case of 3D imaging sequences, three navigator measurements can be used to measure the general spatial displacement of the motion occurring.

When the next phase-encoding gradient is not uniquely determined by the above selection methods, as, for example, when only permissible ranges for the time integral of the next phase-encoding gradient are determined, further selection criteria can be optionally applied in order to make this selection unique. According to one such optional criterion and in order to achieve further reductions in imaging times, any permissible phase encoding gradient that has not yet been applied can be next applied in a priority ordering. In one such priority ordering, the next phase-encoding gradient is that with the smallest, permissible, time integral that has not yet been applied. Alternately and less preferably, phase-encoding gradients can be applied in a pre-determined temporal order (such as low to high or centric) as soon as permissible. Of course, a phase-encoding gradient that has been previously applied is not applied again.

Figure 4:
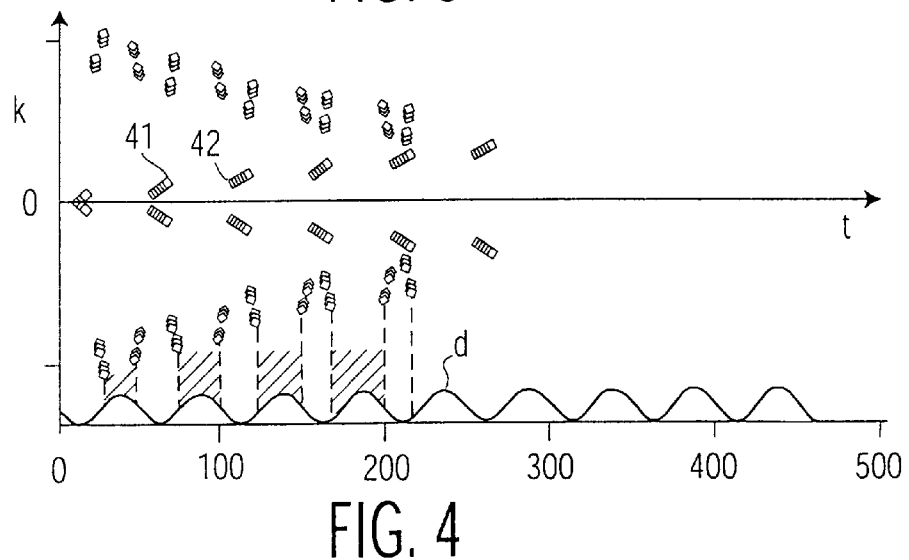
FIG. 4 illustrates an exemplary ordering of MR signals acquired according to the present invention.

FIG. 4 illustrates how the described adaptive gating methods disorder the acquisition of MR signals. Therein, the time integral of the phase-encode gradient, k, is represented along the vertical axis, and time, or the number of excitations of nuclear magnetization, is represented along the horizontal axis. Just above the horizontal axis the displacement, d, of the moving part of the patient being imaged is illustrated. Here, MR signals, represented by small overlapping squares, are acquired whenever permitted by the instantaneous state of motion but with lower time-integral gradients having priority. Clearly, MR signals are generally acquired in no particular order, and, in fact, MR signals that are adjacent in k-space can be acquired at widely differing times during image data acquisition. For example, although MR signals 41 and 42 are adjacent in k-space, their acquisition is separated by many excitation times during which other MR data is acquired. Similarly, in the case of 3D imaging, nearby rows of data are not necessarily acquired at nearby times. Accordingly, if the strengths of MR signals so acquired are not controlled, unacceptable and rapid modulations will be imposed in k-space causing image artifacts.

In order to minimize or substantially eliminate such image artifacts, according to the next steps of the present invention, the strengths of the next signals to be generated are adaptively selected so that the total signal strength distribution throughout k-space will be have a shape pre-determined to minimize artifacts. MR signal strength can be controlled by selecting the angle (α) to flip the longitudinal magnetization, or equivalently, by selecting the power of the RF pulse to be applied for exciting the MR signal. It is generally known (as described below) how to achieve a particular pre-determined signal strength from knowledge of the MR protocol and its parameters by flipping the longitudinal magnetization by a determined flip angle, α, using a determined RF pulse power.

Figure 5:
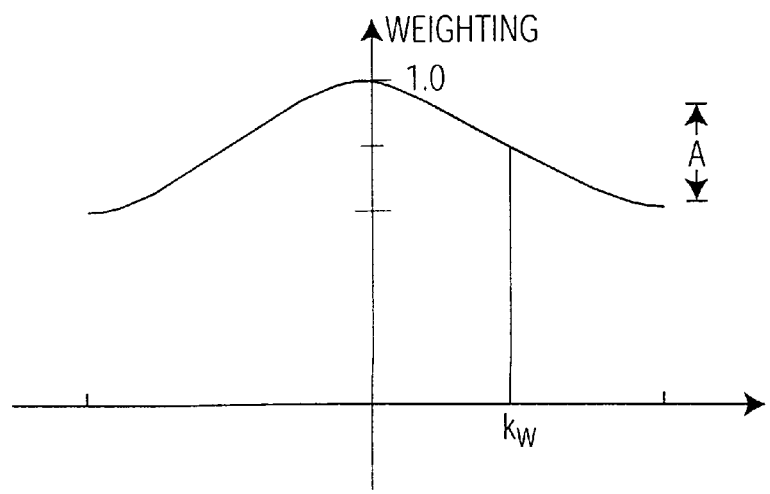
FIG. 5 illustrates a preferred k-space modulation function of the present invention.

Using such knowledge, the overall MR signal strength is chosen to have a pre-determined smooth variation throughout k-space according to an arbitrary function. In a preferred embodiment, signal strength distribution in k-space is chosen to tradeoff image resolution against image noise in a clinically useful manner. This is achieved by a signal strength distribution which is highest at the center of k-space, where the MR signals define major image features and have the highest signal-to-noise ratio (SNR), and lowest the at edges of k-space, where the MR signals define only fine image details but have the lowest SNR. Such a distribution retains major image features while reducing overall image noise at the expense of a blurring (or spreading) of the point spread function More preferably, this distribution is according to a circularly symmetric function that smoothly and monotonically declines from a maximum at the center of k-space to a minimum at its periphery. A Gaussian function of the distance from the center of k-space, |k|, is a most preferred distribution, since its only artifact is a known Gaussian broadening of the point spread function FIG. 5, in which the signal strength is along the vertical axis and the distance from the center of k-space is along the horizontal axis, illustrates an exemplary preferred Gaussian distribution with the parameters amplitude (A) and half-width ($k_w$). These parameters can be adjusted (experimentally) in each imaging situation to provide the most useful tradeoff between image resolution and image noise. This invention is adaptable to other similar signal strength distribution functions.

In another embodiment, the overall MR signal strength is chosen to be constant throughout k-space. This alternative obtains the highest resolution, by equally sampling all k-space information, but also retains the most image noise, by retaining the higher SNR signals from the periphery of k-space at full strength.

Therefore, in detail, once the time integral of the next phase-encoding gradient has been selected in dependence on the instantaneous state of motion, the MR signal strength is then selected (by choosing the flip angle or, equivalently, the power of the next RF pulse) in dependence on the selected time-integral in order to achieve the pre-determined signal strength distribution in k-space. For example, since this time integral determines the distance of the MR data from the center of k-space, the preferred signal strength, and flip angle, can be immediately selected from the preferred distribution function, for example, from the function of FIG. 5. Alternately, the k-space signal strength distribution can be expressed directly in terms of the instantaneous state of motion, and the time integral of the phase-encoding gradient can be then selected simultaneously with the flip angle. This alternative is possible, for example, where the adaptive gating method uniquely determines a time integral from a given instantaneous state of motion, or where the k-space distribution is expressed in terms of the gating (or displacement) threshold for each portion of k-space.

Further embodiments of the last steps for achieving pre-determined MR signal strengths by selecting the RF flip angles (α) are now described with reference to certain known details of the generation of MR signals. In these embodiments, flip angles are selected in further dependence on the expected state of the longitudinal magnetization just before an RF pulse, in order that the actually generated signal strength approximate more closely the pre-determined or preferred signal strength distribution in k-space.

In one such embodiment, the flip angles are selected to take into account the decrease in net longitudinal magnetization that occurs during an imaging sequence, such as during the L repeats of the final imaging sequence illustrated in FIG. 2A. In detail, since the measured MR signal is the Fourier transform of the spatial distribution of the transverse magnetization present when the MR signal is measured, it is known that the signal strength is approximately proportional to both the transverse magnetization just after an exciting RF pulse ($M^n_{T,after}$) and also to an MR-protocol-dependent factor describing the evolution of the transverse magnetization between its excitation and its measurement. The transverse magnetization generated by an exciting RF pulse is (assuming no residual transverse magnetization) known to be approximately described by the following rotation:

$$M^n_{T,after} = M^{n-1}_{L,before} \sin(\alpha_n) \tag{1}$$

$$M^n_{L,after} = M^{n-1}_{L,before} \cos(\alpha_n) \tag{2}$$

Here, $\alpha_n$ is the n'th flip angle of the RF pulse; $M^n_{L,after}$ is the longitudinal magnetization at the n'th repetition of imaging data collection just after the exciting RF pulse; and $M^{n-1}_{L,before}$ is the longitudinal magnetization at the n−1'st image data collection just before the RF pulse.

From Eqns. 1 and 2, it is seen that the RF pulse (with flip angle α) not only excites the traverse magnetization but also decreases longitudinal magnetization. Therefore, when selecting flip angles, it is preferable to take into account decreases in the net longitudinal magnetization due to this known effect in order that the actual signal strength approximate more closely the pre-determined or preferred signal strength distribution in k-space.

In one case, where the repeat time (TR) of the MR sequence is long compared to the longitudinal relaxation time ($T_1$), that is where TR>>$T_1$, then the longitudinal magnetization will always relax to its equilibrium value (determined by the strength of the steady magnetic field) before the next image data acquisition. In this case, no adjustment of the flip angles in dependence on changing longitudinal magnetization is necessary. Such slower imaging sequences are not the principal application of the present invention.

The preferred application of the present invention is to fast imaging of moving parts of a patient, and here preferably TR is as small as possible, typically TR is 10 msec. or less and TR<<$T_1$, where $T_1$ is typically at least 1000 to 1200 msec. (Herein, "<<" denotes being a factor of 0.25 less, or more preferably a factor of 0.10 less, or even more preferably 0.01 or less.) Then, still neglecting the effects of residual traverse magnetization, since little or substantially no change in the longitudinal magnetization occurs during an MR imaging sequence, the change of longitudinal magnetization during N repeats of image data collection sequences is given approximately by the following.

$$M^n_{L,before} = \cos(\alpha_n)\cos(\alpha_{n-1}) \ldots \cos(\alpha_1)M_L \tag{3}$$

when n is small (and also nTR<<$T_1$). Typically, an initial flip angle, $\alpha_1$, is between 10° and 30°. Since the longitudinal magnetization is drained away during image data acquisition, guided by Eqn. 3, it will be apparent how the $\alpha_n$ must be gradually increased from the initial flip angle to maintain a pre-determined signal strength. Detailed selection of flip angles for individual image sequences used in this embodiment can be refined by experimental adjustment.

In this embodiment, the effects of coherent traverse magnetization remaining at the end of each image data acquisition (known herein as "residual" traverse magnetization) have been neglected. These effects can be ignored without affecting the accuracy of MR signal strength determination, when, for example, sequence repeat time (TR) is great compared to spin-spin relaxation time ($T_2^*$), that is when TR>>$T_2^*$, so that transverse magnetization substantially relaxes during each image data acquisition. These effect can also be neglected when the MR protocols used include RF or gradient spoilers present at the end of each image data acquisition that destroy the coherence of the transverse magnetization. Even where residual transverse magnetization is present, these effects can still be ignored when less accuracy is acceptable.

In further aspects of this embodiment, for increased accuracy of MR signal strength determination, the effects of traverse magnetization can be taken into account. It is well known that when residual transverse magnetization is present in an MR sequence, it will be partially rotated by the next RF pulse into the longitudinal direction that will then affect the signal strength of subsequent MR signals. In this case, accounting for the expected longitudinal magnetization with increased accuracy becomes more involved.

When coherent transverse magnetization remains at the end of image data acquisition (for example, if TR is of the same order of magnitude as or smaller than $T_2$) it is possible to account for account for the expected longitudinal magnetization by using a steady state sequence, that is one in which the magnetization components just before each imaging data acquisition are substantially constant in time. This can be achieved by proper phasing of the RF excitation pulses, by rewinder gradients (as illustrated in FIGS. 2A–B), and by particular sequence timings.

Alternately, when the residual magnetization is present in a non-steady state, longitudinal magnetization can be predicted in a general fashion by incrementally integrating the Bloch equations. See, generally, Vlaardingerbroek et al., 1996, *Magnetic Resonance Imaging: Theory and Practice*, Springer-Verlag, especially chaps. 4 and 5. High speed processing using the known already-applied RF and gradient pulses can permit such general prediction of longitudinal magnetization and more accurate determination of MR signal strength in accord with the pre-determined k-space distributions of this invention. In this alternative, operation of the present invention can be optimized for any tissues whatever its $T_1$ value.

For example, in one application of the present invention to cardiac imaging, eight repeats of a rapid gradient field-echo image data acquisition sequence (the grouping of repeats being referred to as a "shot") follow measurement of the instantaneous state of motion, such as by an initial navigator sequence. The $T_R$ of each data acquisition sequence is preferably short, 8–10 msec. or less.; and the time between shots will be of the order of one heartbeat. For blood, $T_1$ is approximately 1000–1200 msec, and T2 is approximately 240–260 msec. Therefore, during each shot (of about 70 msec) there will be both very little relaxation of the longitudinal magnetization and substantial residual transverse magnetization. In this application, residual transverse magnetization is preferably taken into account by spoiling, steady state sequences, or general prediction using the Bloch equations. With less accuracy, residual transverse magnetization can simply be neglected, and the flip angles can be selected as guided by, for example, Eqn. 3.

Finally, in the final steps of the methods of the present invention, the selected flip angles (or, equivalently, the selected RF powers) and selected phase-encoding gradients are applied by an MR apparatus to the part of the patient being imaged, and the generated MR signals received. Image data acquisition is repeated until sufficient data is acquired for image reconstruction. Image reconstruction is then according to known methods, for example by Fourier transformation.

Although the present invention has been described in detail primarily in an implementation utilizing gradient-echo type MR sequences, it is not so limited as described above. In particular, it can also be applied to type spin-echo and hybrid type sequences. Typically, the spin-echo refocusing pulse is 180°, but if less than 180° the signal strength is correspondingly and controllably reduced. For spin-echo sequences, phase-encoding gradients can be selected as above. Since signal strengths of MR signals generated in spin-echo sequences can be similarly controlled by adjusting the flip angle of the echo refocusing RF pulse, flip angles can be selected substantially as above in order to minimize irregular signal strength modulations in k-space.

For further MR protocols which can be applied in this invention, see, generally, Stark et al., 1992, *Magnetic Resonance Imaging*, Mosby.

Implementations of the Methods the Present Invention

Lastly, exemplary hardware and software implementations of the methods of the present invention are described.

Figure 6:
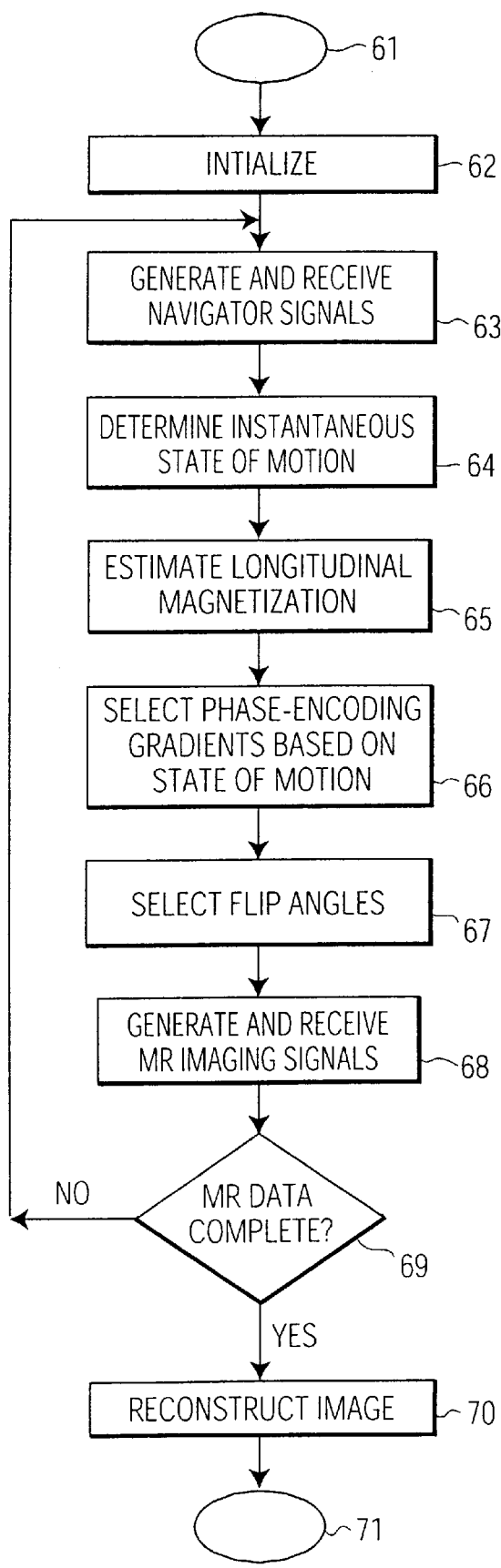
FIG. 6 illustrates a preferred implementation of the methods of the present invention.

FIG. 6 illustrates a preferred method for practicing the invention as implemented by software loaded into the control unit of an MR apparatus. The process starts at step 61 and initializes the MR apparatus in known manners at step 62. At steps 63 and 64, the instantaneous state of motion of the moving part of the patient being imaged is measured by generating and receiving one-dimensional MR navigator signals, for example, as illustrated in the initial portions of FIGS. 2A and 2B. The instantaneous displacement is determined from these signals by, for example, cross-correlating the spatial distribution of the nuclear magnetization extracted from the received navigator signals with a reference distribution for a reference position of the part.

At step 65, the longitudinal magnetization is estimated by the more or less exact methods described above. For example, approximations neglecting residual transverse magnetization described above can be used, or steady state sequences can be used, or alternatively, the course of the longitudinal can be tracked by integrating the Bloch equations.

Next, at step 66, the phase-encoding gradients to be applied in the next one or more MR image data acquisitions are selected, for example, according to the motion adaptive gating methods described above. It is to be understood, however, that the present invention is adaptable to any method for selecting the next phase encoding gradient, and it is particularly advantageous when the results of such selecting cause data closely spaced in k-space to be acquired at remote times during the entire image data acquisition.

From the estimated longitudinal magnetization and from the selected next phase-encoding gradients (or the measured instantaneous displacement), at step 67, flip angles can be selected that achieve the desired pre-determined k-space distribution of this invention. Alternately, steps 66 and 67 can be combined so that the next phase-encoding gradient and the associated flip angles can be jointly selected.

Finally, at step 68, the selected phase-encoding gradients and flip angles (or, equivalently, RF power) are applied by the MR apparatus to the part being imaged. Exemplary MR imaging sequences are illustrated in the final portions of FIGS. 2A and 2B. The generated MR signals are received, and if the MR dataset is not complete, steps 63–68 are repeated by step 69. If the dataset is complete, the MR image is reconstructed at step 70, and the method terminates at step 71. In a further alternative, when the dataset is complete, the method can proceed to measure again the next best phase-encoding gradient and average it with the previously measured signal. In this fashion, the signal-to-noise ratio of the dataset can be increased in a highly effective manner.

One of skill in the art, in view of the above description, will recognize numerous equivalent hardware and software implementations for performing the methods of this inventions. It is intended that the appended claim encompass such recognized equivalent implementations.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A magnetic resonance (MR) method for imaging a moving object with reduced motion artifacts, the method comprising:

measuring the instantaneous state of motion of the object present in an examination zone, selecting phase-encoding gradients wherein the time integrals of the selected phase-encoding gradients depend at least in part on the measured instantaneous state of motion, selecting flip angles, wherein the selected flip angles depend at least in part on the previously selected phase-encoding gradients or on the measured instantaneous state of motion, generating MR signals from the object by applying RF pulses to excite nuclear magnetization with the selected flip angles and by applying the selected phase-encoding gradients, and reconstructing an MR image from the generated MR signals.

2. The method of claim 1 wherein the object moves in a repetitive manner.

3. The method of claim 1 wherein the selected phase-encoding gradients depend on previously selected phase-encoding gradients, and wherein a phase encoding gradient is selected only if that phase-encoding gradient has not previously been selected.

4. The method of claim 1 wherein the instantaneous state of motion of the object is represented by a measured instantaneous displacement in a pre-determined direction, and wherein the selected phase-encoding gradients are in the pre-determined direction.

5. The method of claim 4 wherein the step of measuring comprises generating and receiving MR navigator signals.

6. The method of claim 4 wherein a phase-encoding gradient is selected only if the measured displacement does not exceed a threshold value of the displacement, wherein the threshold value of the displacement depends in an increasing manner on the time integral of the phase-encoding gradient.

7. The method of claim 1 wherein the instantaneous state of motion of the object is represented by instantaneously measured displacements in two pre-determined directions, and wherein the phase-encoding gradients are in the two predetermined directions.

8. The method of claim 1 wherein the selected flip angles depend on the previously selected time integrals of the phase-encoding gradients so that the signal strength of the excited MR signal varies smoothly in k-space according to an arbitrary function.

9. The method of claim 8 wherein the smooth variation in k-space is a constant signal strength.

10. The method of claim 8 wherein the smooth variation in k-space is represented by a circularly symmetric function that is monotonically decreasing from the center to the periphery of k-space.

11. The method of claim 10 wherein the smooth variation in k-space is a Gaussian having a maximum at the center of k-space.

12. The method of claim 1 wherein the selected flip angles depend also on the previously measured instantaneous state of motion.

13. The method of claim 1 further comprising determining the expected state of nuclear magnetization prior to application of the next RF pulse, and wherein the selected flip angles depend also at least in part on the determined expected state of nuclear magnetization.

14. The method of claim 13 wherein a plurality of MR signal generating steps are grouped together into a shot.

15. The method of claim 13 wherein determining the expected state of nuclear magnetization comprises determining the expected state of longitudinal nuclear magnetization neglecting residual transverse nuclear magnetization.

16. The method of claim 13 wherein determining the expected state of nuclear magnetization comprises determining the expected state of longitudinal nuclear magnetization considering residual transverse nuclear magnetization.

17. The method of claim 1 wherein MR signals are generating with a repeat time which is much less than the relaxation time of longitudinal nuclear magnetization.

18. A magnetic resonance (MR) apparatus for acquiring images of a moving part of a patient placed in an examination zone of the MR apparatus with reduced motion artifacts, the apparatus comprising:

a main magnet system for generating a steady magnetic field in the examination zone, a gradient magnet system for generating temporary gradient magnetic fields in the examination zone, a radio frequency (RF) transmitter system for generating RF pulses in the examination zone, an RF receiver system for receiving MR signals from the examination zone, a reconstruction unit for reconstructing an image of the region of the patient from the received MR signals, a control unit for generating signals controlling the gradient magnet system, the RF transmitter system, the RF receiver system, and the reconstruction unit, wherein the control unit generates signals causing measurement of the instantaneous state of motion of the object present in an examination zone, selecting of phase-encoding gradients wherein the time integrals of the selected phase-encoding gradients depend at least in part on the measured instantaneous state of motion, selecting of flip angles, wherein the selected flip angles depend at least in part on the previously selected phase-encoding gradients or on the measured instantaneous state of motion, generating of MR signals from the object by applying RF pulses to excite nuclear magnetization with the selected flip angles and by applying the selected phase-encoding gradients, and reconstructing of an MR image from the generated MR signals.

19. A computer readable media carrying encoded program instructions for causing a programmable MR apparatus to perform the method of claim 1.

* * * * *